United States Patent [19]

Michaels et al.

[11] 4,442,206

[45] Apr. 10, 1984

[54] METHOD OF USING ISOTROPIC, POROUS-WALL POLYMERIC MEMBRANE, HOLLOW-FIBERS FOR CULTURE OF MICROBES

[75] Inventors: Alan S. Michaels, New York, N.Y.; Channing R. Robertson, Stanford; Stanley N. Cohen, Portola Valley, both of Calif.; Douglas S. Inloes, Clayton, Mo.; William J. Smith, Stanford, Calif.

[73] Assignee: Stanford University, Stanford, Calif.

[21] Appl. No.: 489,609

[22] Filed: May 4, 1983

Related U.S. Application Data

[63] Continuation of Ser. No. 179,590, Aug. 21, 1980, abandoned.

[51] Int. Cl.³ .................. C12P 21/00; C12N 9/00; C12M 3/00
[52] U.S. Cl. ..................... 435/68; 435/161; 435/171; 435/174; 435/183; 435/284; 435/813
[58] Field of Search ............... 435/68, 161, 182, 183, 435/171, 174, 261, 240, 241, 284, 813, 836; 210/606, 610, 620, 500.2, 321 R

[56] References Cited

U.S. PATENT DOCUMENTS

| 3,580,840 | 5/1971 | Uridil | 435/261 |
|---|---|---|---|
| 3,767,790 | 10/1973 | Guttag | 435/182 |
| 3,827,565 | 8/1974 | Matsumura | 435/182 |
| 3,883,393 | 5/1975 | Knazek et al. | 435/240 |
| 3,911,140 | 10/1975 | Osborne et al. | 435/139 |
| 4,266,026 | 5/1981 | Breslau | 435/182 |
| 4,391,912 | 7/1983 | Yoshida et al. | 435/241 |

OTHER PUBLICATIONS

Kan et al., "Urocanic Acid Production Using Whole Cells Immobilized on a Hollow-Fiber Reactor", *Biotech. & Bioeng.*, vol. 20, pp. 271–320, 1978.
Webster et al., *Biotechnology and Bioengineering*, vol. 21, Abstract, pp. 1725–1748, 1979.
Webster et al., *Biotechnology and Bioengineering*, vol. 20, Abstract, pp. 1541–1556, 1978.
Webster et al., *Chemical Engineering Science*, vol. 34, 1979, pp. 1273–1282.
Porter, M. C., *Biotechnology and Bioengineering Symposium No. 3*, "Applications of Membranes to Enzyme Isolation and Purification", 1972, pp. 115–130.

*Primary Examiner*—Raymond N. Jones
*Assistant Examiner*—Elizabeth J. Curtin
*Attorney, Agent, or Firm*—Flehr, Hohbach, Test, Albritton, & Herbert

[57] ABSTRACT

Hollow fiber reactors for growing microbial cells. Isotropic hollow fibers are supported in a housing inoculated with cells. Nutrient medium passing through the lumen undergoes a pressure drop resulting in radial convective flow: the nutrient medium flows outwardly from the lumen into the surrounding area adjacent the entry port and fluid surrounding the hollow fiber flows into the lumen adjacent the exit port. With the efficient distribution of nutrients and removal of product, high cell densities are achieved providing for high product yields per unit reactor volume.

11 Claims, 3 Drawing Figures

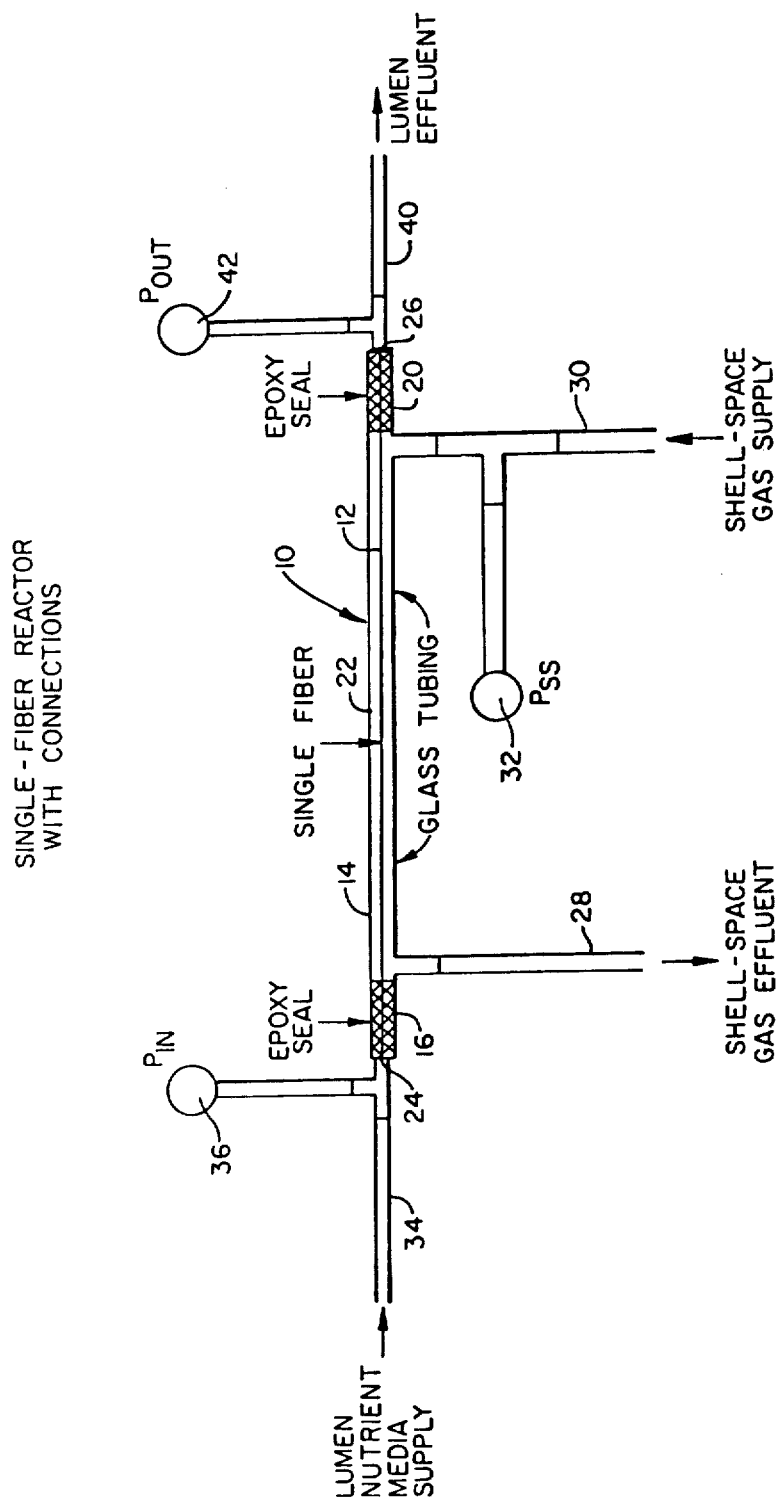
FIG.—1.

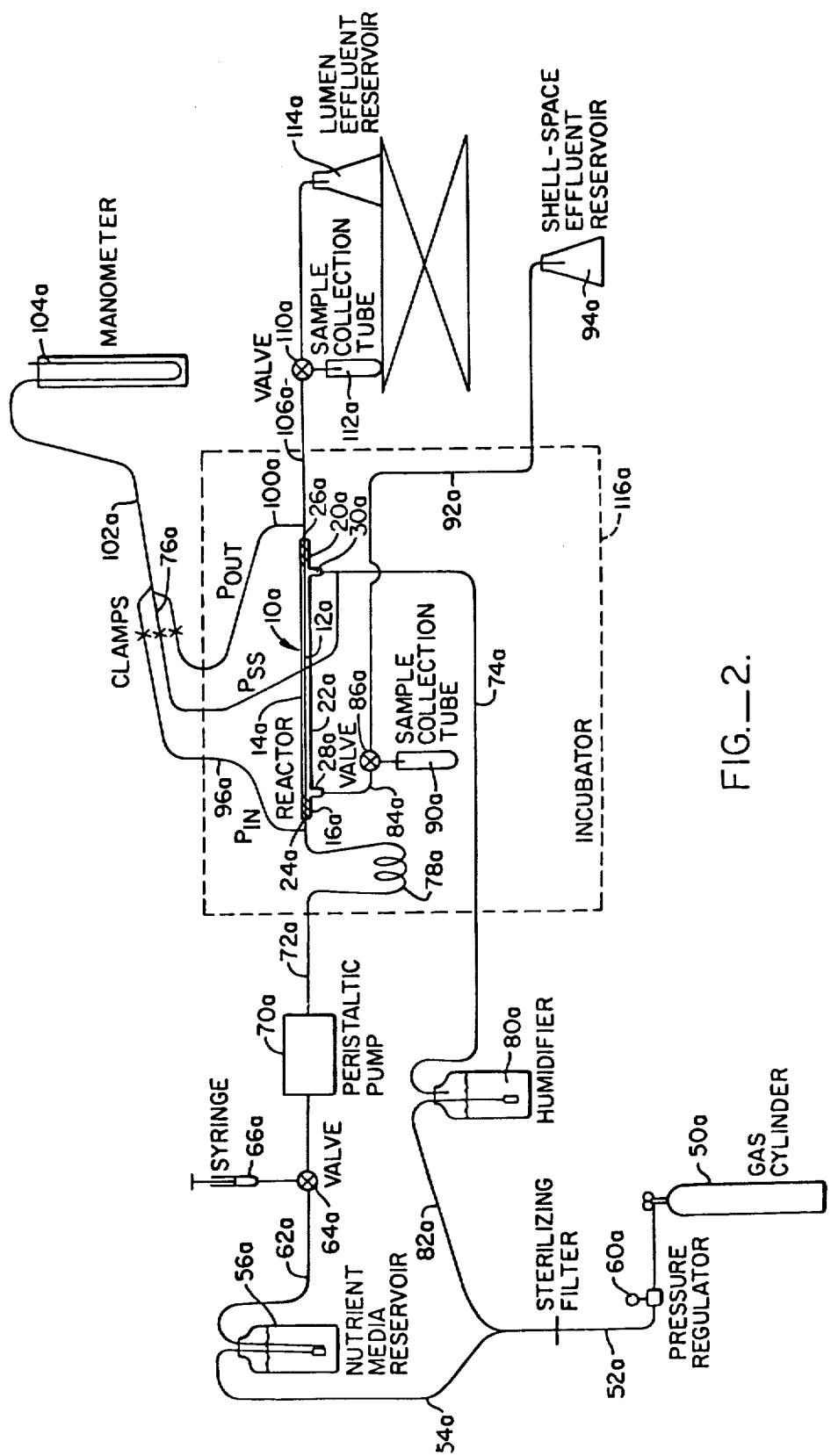
FIG._2.

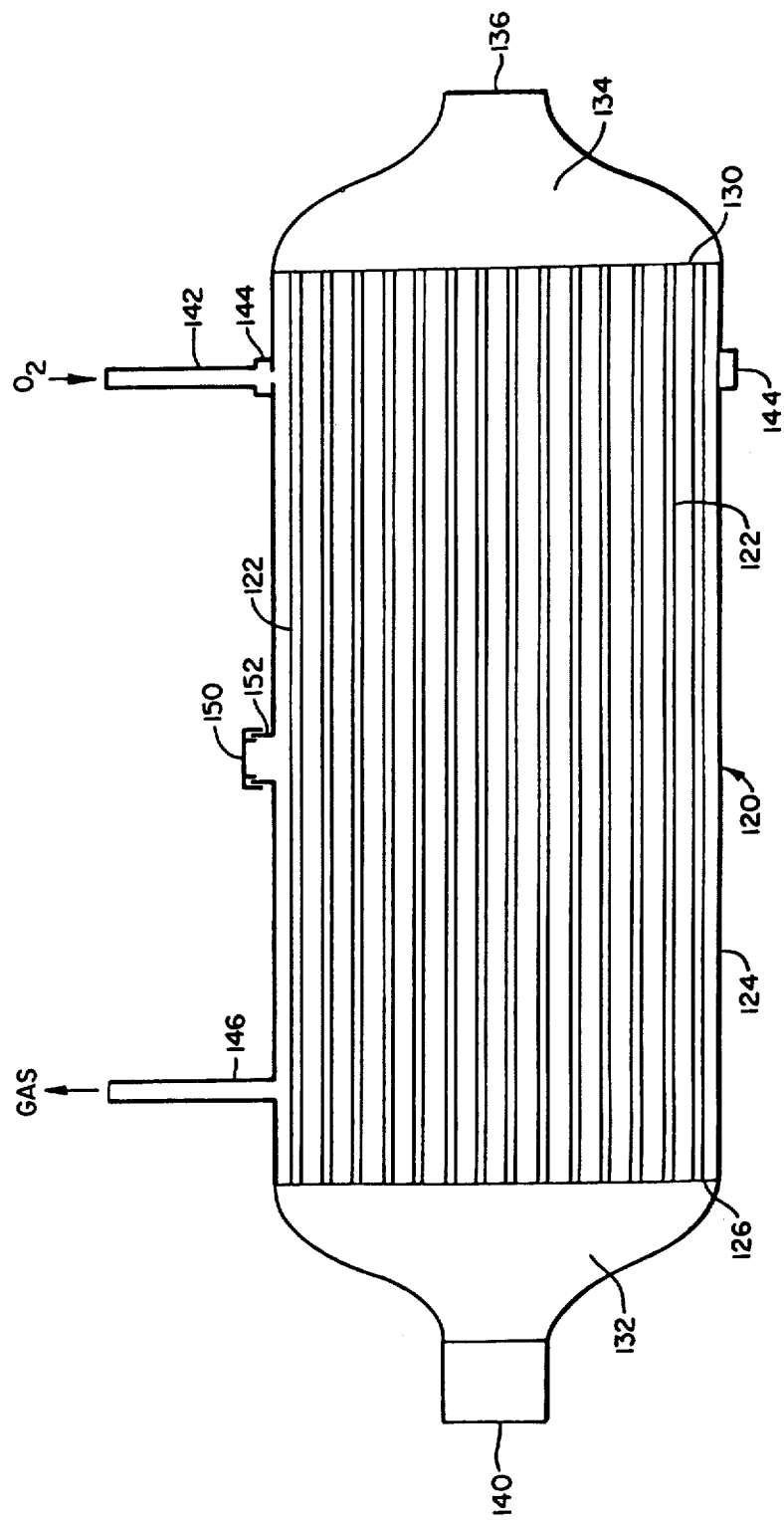

METHOD OF USING ISOTROPIC, POROUS-WALL POLYMERIC MEMBRANE, HOLLOW-FIBERS FOR CULTURE OF MICROBES

This is a continuation of application Ser. No. 179,590 filed Aug. 21, 1980, now abandoned.

BACKGROUND OF THE INVENTION

1. Field of the Invention

Despite the ancient character of the growth of single cells, particularly yeast in fermentation and more recently unicellular organisms in the production of antibiotics, there have been few significant advances in the design of reactors for the use of single cells in commercial processes. In growing cells efficiently to produce a product which is to be isolated, a large number of considerations are involved.

For high efficiency, it is desirable that there be a high cell density so that a substantial proportion of the volume of the reactor is filled with closely packed viable cells. In order to obtain high densities, it is necessary to have efficient distribution of nutrients, so that substantially all of the cells are bathed in a growth supporting nutrient medium. Both economics and cell viability put a limit on the amount of nutrients that can be introduced into the nutrient medium. Furthermore, product will frequently inhibit cell production of the product. Therefore, an efficient means must be provided for continuously removing product to maintain a concentration level of the product below a predetermined level. In addition, cells are fragile and can easily be broken. Dead cells remaining in the reactor reduce the efficiency of the reactor by occupying space which could otherwise be occupied by viable cells.

A further consideration is obtaining the product cell free. That is, if the product containing medium exiting the reactor includes cells, these cells must be removed. Employing microfilters creates numerous problems in slowing down the flow of the liquid, becoming clogged by cells, and adding significant capital costs and processing costs.

It is therefore desirable to provide new and improved reactors for growing single cells, particularly microorganisms, such as bacteria and yeast, to provide for economic and efficient production of microbiological products.

2. Description of the Prior Art

U.S. Pat. No. 3,580,840 describes the method and apparatus using microorganisms for sewage treatment employing a porous membrane. U.S. Pat. No. 3,767,790 teaches microorganism entrapment for controlled release. See also U.S. Pat. No. 3,860,490. U.S. Pat. No. 3,875,008 teaches microorganism encapsulation in a hollow filament. U.S. Pat. No. 4,148,689 teaches entrapment of microorganism in a gelled sol.

SUMMARY OF THE INVENTION

Method and apparatus are provided for microbiological transformation of a nutrient stream. The microbiological reactor employs an isotropic hollow fiber in a housing. The housing contains cells, usually proliferative, surrounding the hollow fiber. Nutrient medium continuously passing through the lumen exits from the pores of the hollow fiber adjacent the entry port to continuously replenish the nutrients in the reactor. Partially spent nutrient medium containing product is withdrawn through the hollow fiber pores from the volume surrounding the hollow fiber near the exit port. Radial convective flow results from the small pressure differences in the lumen at the entry and exit ports, as compared to the liquid pressure external to the hollow fiber. As a result of efficient distribution of nutrients and removal of products, high cell densities can be achieved to provide for efficient product formation per unit reactor volume.

BRIEF DESCRIPTION OF THE DRAWINGS

FIG. 1 is a schematic view of a single fiber reactor;

FIG. 2 is a flowchart of a single fiber reactor providing for monitoring the streams entering and exiting from the reactor; and FIG. 3 is a cross-sectional view of a multifiber reactor.

DESCRIPTION OF THE SPECIFIC EMBODIMENTS

Novel reactors and method employing the reactor are provided for microbiological transformations. The reactors employ at least one, normally a plurality of isotropic porous wall hollow fibers, which are mounted in a closed housing providing for the introduction and removal of fluid media from the lumens of the hollow fibers as well as the housing shell space. The reactors are employed for the maintenance and growth of cells, particularly single cells, such as microorganisms, proliferative cells, such as tumor cells, and proliferative cells derived from tissue cells, such as hybridomas, and tissue cells.

In carrying out the method, the cells are inoculated into the fluid in the space surrounding the hollow fibers, while the nutrient medium stream is directed through the lumen or internal volume of the hollow fibers. The nutrients and substrates pass through the pores of the hollow fiber wall into the surrounding volume in the housing or shell space. Due to the pressure drop across the length of the hollow fiber, radial convective currents are set-up in the surrounding volume. The pressure gradient in the lumen results in a maximum rate of flow outwardly from the lumen at the entry port and a maximum rate of flow inwardly into the lumen at the exit port. Thus, a natural flow of nutrients to the cells and product away from the cells is achieved, ensuring the continuing replenishment of nutrient in the cell containing shell space and the continuous removal of product from the shell space.

The microporous hollow fibers which are employed will generally have an outer diameter of less than about 1 mm, usually less than about 0.75 mm and greater than about 0.25 mm, usually greater than about 0.4 mm. The diameter of the lumen may be varied widely, usually being about 25% of the total diameter, and may be as high as 90% or more. Wall thicknesses will generally range from about 15 to 100 microns, more usually from about 20 to 50 microns.

A number of considerations will affect the size of the lumen and wall of the hollow fiber. Among these considerations are the desired rate of flow of the nutrient medium; the pressure gradient; maintenance of a supportive nutrient medium for the cells in the external volume; concentration of product; reactor volume efficiency and the like. The size and number of pores will also affect these parameters.

The porosity will be at least about 25% of the wall volume and not more than about 50% of the wall volume. Preferably, the wall will be relatively uniform having pores with the largest cross-sectional dimension being less than about 1 micron, usually less than about 0.5 microns, with the cross-section having as its smallest dimension at least 0.005 microns, more usually at least about 0.01 microns. The pore size is governed by the following considerations: The rate of diffusion of nutrients and products through the pores; molecular separability inhibiting passage of molecules above a predetermined molecular weight through the pores; and the inhibition or exclusion of cells into the lumen. Therefore, while the values given above are directed to small microorganisms, larger pore sizes could be employed where larger cells are being grown. Thus, one would employ a pore size to exclude the cells from entering the pore and as large as possible to allow for the rapid flow of nutrients and products in and out of the lumen.

A wide variety of materials may be employed for the hollow fiber. For the most part, the hollow fibers will be polymeric materials, which may be hydrophilic or hydrophobic. Particularly, polyolefins, e.g. polypropylene, either high or low density, can be used. The polymers may be modified, either before or after formation of the hollow fibers, to change the chemical and physical properties of the polymer.

Of particular interest is a polypropylene hollow fiber supplied by Celanese corporation under the trademark Celgard. The fibers are manufactured by melt spinning and stress-induced microcracking of polypropylene. The wall consists of a microporous matrix of polymer fibrils of about 40% porosity and containing slit-like pores of dimensions approximately 2.0 by 0.02 microns. The wall is freely permeable to liquids and gases, but virtually completely impermeable to cells or particles of dimensions greater than about 0.02 microns.

Desirably, the hollow fiber should be capable of withstanding elevated pressures and mildly elevated temperatures. By employing elevated pressures, the concentration of oxygen or other gases can be enhanced in the fluid medium.

The thickness of the wall is sufficient to provide structural strength, but should not unduly extend the pathlength of the pores. However, the pathlength should be sufficient to insure the complete exclusion of cells from the lumen.

The length of the hollow fiber in the reactor can be varied widely subject to a number of considerations which have already been mentioned. The primary concern is that the perfusion of nutrients throughout the reactor is sufficient to maintain growth at every point. By nutrients is intended to include not only substrates which might have limited solubility in the aqueous nutrient medium, but also gases of limited solubility, particularly oxygen. With gases, it is feasible to introduce the gases into the shell space, as well as into the lumen. Therefore, to the extent that the amount of oxygen or other gas would be limiting, one can reduce the dependency on obtaining the gas from the lumen by the supplementary introduction into the shell space. The amount of nutrient required will depend upon the particular cell type, the rate of growth, the sensitivity of the cell to high nutrient concentrations, the rate of flow, the pressure drop across the hollow fiber, the rate of removal of product, the effect of product concentration on the inhibition of product production, and the like. In each instance, therefore, the length will be chosen to optimize the desired result. For the most part, the hollow fiber length will be at least about 1 cm, more usually at least about 5 cm, and less than about 100 cm, usually less than about 50 cm.

Single reactors may be employed or a plurality of reactors in tandem. After processing, nutrient streams may be recycled, side streams returned, or the like. The reactor may be employed batchwise or continuously, usually continuously.

While a reactor having a single hollow fiber may be employed, for the most part a plurality of fibers will be employed in a single housing or shell. The housing will enclose the hollow fibers so that the fibers are washed in the nutrient medium which flows or diffuses out of the pores of the hollow fiber. One or more ports may be provided in the shell for introducing materials external to the fibers, for sampling, for removal of gases, for isolation of product containing spent nutrient medium, or the like. The housing may also be used for maintaining a pressure differential between the lumen and the shell space.

The organization of the hollow fibers in the shell will be governed by the efficiency of perfusion of the nutrient medium in the shell space, the length of the hollow fiber, the cell packing, the desired rate of production of product, the nature of the cells, and the like. Usually, the hollow fibers will occupy from about 10 to 75% of the total volume in the reactor.

The reactor will be provided with means for maintaining a pressure differential between the pressure of the nutrient medium entering the lumen and the pressure in the shell space. This can be achieved by pumping the nutrient medium at a positive pressure above atmospheric into the lumen, while maintaining the pressure in the shell space below the entry pressure of the nutrient medium. In many situations it will be desirable that the entry pressure and shell space pressure be above atmosphere.

The pressure gradient and, therefore, the pressure at the lumen exit, will be controlled by a number of factors: lumen diameter and length; nutrient medium flow rate; viscosity of the nutrient medium; entry pressure; pressure of the nutrient medium; and pressure in the shell space. By appropriate choice of the above parameters, the rate of radial convective flow can be controlled. In addition, one can control the exit pressure by providing a vacuum or back pressure. Therefore, the subject system allows for widely varying the radial convective flow to ensure perfusion of the nutrient medium through high cell density packing about the hollow fibers. Usually, the maximum pressure differential between the lumen and the shell space will be less than about ten percent, usually less than about five percent of the pressure in the lumen.

A wide variety of cells, particularly microorganisms, may be grown in the reactor. Among microorganisms, bacteria, yeast, and fungi would be the most common. Not only can naturally occurring cells be employed, but also cells which have been modified by conjugation, hybrid DNA, fusion, or the like. Among the cells which may be grown in the reactor other than microorganisms are various mammalian cells which be cultured in vitro, particularly tumor cells and hybridomas.

The nutrient medium employed will be dependent upon the cells involved and the product desired or purpose for the reactor. For example, the nature of the nutrient medium will be adapted to the particular type of cells. Besides nutrients, other substances may be included to support growth and/or cell differentiation or to provide a particular product.

The products which may be produced include natural products such as excreted or non-excreted proteins e.g. enzymes, hormones, lymphokines, toxins, immunoglobulins, or the like, or a non-proteinaceous organic compound resulting from transformation of a substrate, such as by epoxidation, hydroxylation, esterification e.g. acetate, phosphate, uronate, or sulfate, reduction, methylation, etherification with sugars, or the like. Thus, the reactor can act as a source of a wide variety of compounds, either as the natural product, such as a polypeptide or protein, or for transforming a synthetic substrate. Alternatively, the reactor may be used with a variety of effluents from various commercial processing sources, such as chemical processing plants, sewage plants, water treatment plants, or the like.

Besides nutrients provided in the lumen, additional nutrients may be provided in the shell space. Particularly, because of the low solubility of oxygen in water, additional oxygen may be dissolved into the fluid surrounding the hollow fibers. To further enhance oxygen content, the fluid and shell space may be pressurized so that the concentration of oxygen in the nutrient solution is increased.

During operation, the cells substantially fill the volume in the reactor surrounding the hollow fibers. The depth of the cells surrounding the hollow fiber wall will generally be greater than about 50 microns and at packing densities greater than about $10^{12}$ cells/ml. This highly efficient cell growth and packing density is achieved by the efficient distribution of nutrients and removal of product.

For further understanding of the invention, the drawings will now be considered. The reactor 10 is comprised of a single hollow fiber 12 which is centrally extended in a glass tube 14 and sealed at its ends in the tube 14 by seals 16 and 20. Seals 16 and 20 enclose the space 22 in tube 14. The fiber extends to the ends of seals 16 and 20 so as to provide inlet port 24 and exit port 26 for introduction and removal respectively of the nutrient medium. To provide for the opportunity for additional oxygen supply to the shell space 22, as well as for monitoring gas production in the shell space 22, conduits 28 and 30 are connected to the tube 14 in fluid transfer relationship internal to the seals 16 and 20. A manometer 32 is attached to conduit 30 for monitoring the pressure of the gas supply or if desired, the pressure in space 22. Connected to the inlet port 24 is inlet conduit 34 equipped with pressure gauge 36 for monitoring the pressure of the inlet nutrient stream. Outlet conduit 40 is connected to outlet port 26 in fluid receiving relationship and a pressure gauge 42 is mounted on the outlet conduit 40 to provide for monitoring the pressure of the lumen effluent. In addition to providing for the introduction of gas or other materials into the shell space 22, conduits 28 and 30 also provide the opportunity to inoculate the reactor with microorganisms or cells.

FIG. 2 is a diagram of the equipment used in a number of tests. The reactor 10a has single fiber 12a which is sealed in the tube 14a by seals 16a and 20a. Pressurized oxygen is provided by gas cylinder 50a, which is connected by lines 52a and 54a to nutrient medium reservoir 56a. Pressure regulator 60a mounted in line 52a controls the oxygen pressure in line 52a. The oxygen pressure forces the nutrient medium in reservoir 56a into line 62a in which is mounted three-way valve 64a, the remaining arm being fitted with syringe 66a. Line 62a connects with peristaltic pump 70a which controls the flow of the nutrient medium through line 72a to inlet port 24a of hollow fiber 12a. Line 72a has a series of coils 78a to allow for temperature control of the nutrient medium fed to hollow fiber 12a. Side arm 30a of tube 14a is connected by a conduit 74a to shell space sampling conduit 76a and humidifier 80a. The humidifier 80a is connected by means of conduit 82a to line 52a to permit humidified oxygen to be introduced into the reactor shell space 22a. Side arm 28a is connected by means of line 84a to three-way valve 86a which serves to pass the effluent from the shell space 22a into sample collection tube 90a or by means of line 92a to shell-space effluent reservoir 94a.

The nutrient media fed into inlet port 24a by means of line 72a are monitored through line 96a, while the lumen effluent exiting exit port 26a is monitored through line 100a. Lines 76a, 96a, and 100a are all connected to line 102a which is connected to a manometer 104a for monitoring the pressure in the reactor. The nutrient medium of the lumen exiting through exit 26a is connected by line 106a to three-way valve 110a which serves to connect the effluent to sample collection tube 112a or lumen effluent reservoir 114a. For temperature control, the reactor and portions of the components connected to the reactor may be maintained in an incubator 116a indicated by the broken lines.

FIG. 3 depicts a multihollow fiber reactor 120 having a plurality of hollow fibers 122 in a housing or shell 124. The hollow fibers 122 are mounted on manifold discs 126 and 130 which serve to hold the hollow fibers in position while allowing access between the hollow fibers 122 and chambers 132 and 134. Chamber 134 has inlet port 136 while chamber 132 has outlet port 140. Gas inlet conduit 142 connects to gas manifold 144 which distributes the gas evenly about the periphery of the housing 124. Gas outlet 146 is provided to control the pressure in the reactor 120. The reactor is provided with a septum 150 mounted on side arm 152. The septum permits the inoculation of the reactor with cells and removal of samples without disturbing the reactor.

In studying the subject reactor, reactors having from 1 to 100 fibers were studied. In particular, Celgard ®, hollow fibers, available from Celanese corporation, were employed. These porous fibers have pores which are slit-like in shape having dimensions of about 0.04 microns by 0.4 microns. The submicroscopic size of these pores allows the flow of gases and liquids with surface tension less than about 35 dynes/cm. The pore density is about $10^{10}$ pores/cm$^2$ and the porosity is approximately 40%. The fibers employed had an inner diameter of 350 microns and a wall thickness of 25–30 microns.

Two different organisms were studied: One bacterial strain, *Bacillus licheniformis* 749/C and one yeast strain, *Saccharomyces cerevisiae* ATCC No. 4126. The *B. liceniformis* was used for the production of β-lactamase, a bacterial enzyme that cleaves the β-lactam bond in pencillin. The β-lactamase is indicative of a culture's ability to provide a complex biochemical synthesis of a protein in the hollow fiber membrane reactor. The *S. cerevisiae*, was used for ethanol production.

The *B. liceniformis* 749/C is a constitutive producer of β-lactamase, which enzyme has a molecular weight of 28,000 daltons and represents about 2% of the organism's total protein production. The bacteria were grown in LB broth consisting of 10 grams/L tryptone 5 g/L yeast extract and 10 g/L sodium chloride, pH 7 at 37° C. For comparative purposes, the maximum volumetric productivity obtainable in a well aerated shaker flask culture of *B. liceniformis* can be maintained for no more than 24 hrs., occurring during the stationery phase at $10^9$ viable cells/ml and is about 10 units of enzyme per hour per ml of culture broth. (One unit of enzyme hydrolyzes 1 μmole of ampicilloic acid/min. at 30° C., pH 7.0.)

In reporting the results for the hollow fibers, volumetric productivities are given as unit of enzyme produced per hour per total reactor volume. Total reactor volume includes the fiber lumen, fiber wall, and the shell space.

Employing the apparatus described in FIG. 2, *B. licenformis* was inoculated into the shell space of a reactor having Celgard polypropylene fibers. The Celgard fiber was 25 cm long, mounted in a 5 mm I.D. glass tube, with the reactor maintained at a temperature of 37° C. and a pressure of approximately 1 atm. The nutrient medium was saturated with pure oxygen at 1 atm before perfusion through the reactor and humidified oxygen gas at 1 atm. was continuously passed through the reactor shell space following the inoculation procedure.

The cell density was determined, the bacteria growing on the surface of the fiber to a depth of about 60 microns at an estimated packing density of $2 \times 10^{12}$ cells/ml. The rate of production was five units of enzyme per hour per total volume of reactor for four days with a single hollow fiber. Under the same conditions, stable production of three units of enzyme per hour per total reactor volume was obtained continuously for 14 days.

In a second reactor, employing a bundle of 100 Celgard ® fibers in a 5 mm I.D. glass tube of 25 cm length, initial results demonstrated the production of 10 units of enzyme per hour per total reactor volume.

The *S. cerevisiae* culture was studied using from 20 to 40 hollow fibers in a 5 mm I.D. glass tube of 25 cm length. The tube was modified by providing for an additional port closed with a rubber septum cap, so that samples could be periodically withdrawn from the reactor shell space.

The yeast/ethanol fermentations were performed at a temperature of 35° C. and a pressure approximating 1 atm. The culture nutrient medium was a rich medium supplemented with glucose and having the following composition: In 1 L of distilled water, 8.5 g yeast extract; 1.32 g ammonium chloride; 0.06 g calcium chloride; 0.118 Epsom salts; and either 10 g or 100 g glucose to provide for a 1% or 10% solution respectively; with a pH of 6.2. The lower glucose medium was used primarily for yeast growth studies, whereas the more concentrated medium was used for studying ethanol formation. The liquid medium was saturated with air at 1 atm before being pumped through the reactor. In the yeast growth studies, the reactor shell space was continuously flushed with humidified air at 1 atm following inoculation. In experiments designed for maximum ethanol production, after inoculation the shell space was closed off without gas flushing and the cell suspension was allowed to fill the entire shell space. Substantial carbon dioxide gas accumulated, so that during commercial processing, means for venting would be required.

Viable and productive yeast cultures were maintained up to four weeks without any significant reduction in the cultures' ethanol productivity. In initial experiments using Celgard ® fiber bundle reactors, ethanol productivities of about 15 g ethanol per liter reactor volume per hr. were obtained. This value is twice the value of 7 g/L-hr. reported for similar operating conditions using a continuous stir tank fermentor with the same organism. (Cysewski and Wilk, Biotechnol. Bioeng. 18:1297–1313 (1976)).

In another study, ethanol productivities of 29 g/L-hr. and 40 g/L-hr. were reported for the same yeast strain in a continuous stir tank fermentor using atmospheric pressure-cell recycle fermentation and vacuum fermentation at 50 mm Hg respectively. (Cysewski and Wilk, ibid., 19:1125–1143 (1977)). Using both vacuum and cell recycle, the productivity increased to 82 g/L-hr.

Thus, the results obtained with the hollow fiber reactor compare favorably with optimal literature values, despite the absence of optimization of the hollow fiber reactor conditions. The actual product concentration measurement in the reactor effluent was approximately 1% ethanol, which is less than the 4% level reported using a more conventional process. Glucose conversions of 30% were obtained for a single pass through the reactor. In commercial processing, by employing a recycle loop for the reactor effluent, substantially greater conversion efficiencies could be achieved.

The subject invention provides for novel applications of isotropic hollow fibers for cell growth, production of a wide variety of products, chemical processing, as well as waste stream processing. The hollow fiber reactors fulfill many of the requirements for efficient cultivation of cells. Inoculation of cells onto the external surface of the fibers, while nutrient broth flows through the lumen, provides a means for sustaining a concentrated layer of cells on the fiber-exterior, and for removal of products and metabolites from the cell layer by diffusion and flow through the fiber wall into the flowing stream in the lumen.

So long as the pores of the fiber wall are smaller than the cell size, cell leakage into the lumen is obviated. Bundles of the hollow fibers serve as a bed for the growth and maintenance of a concentrated mass of single cells, particularly microorganisms, in the interstices between individual fibers, thus providing a simple, compact "immobilized-cell" bioreactor. By insuring that the path length for molecular diffusion from the lumen to the most distant cell in the interfiber space is maintained small enough to provide an adequate rate of supply of nutrients to the cell population and an adequate rate of removal of products of metabolism from the cell population, the subject hollow fiber reactor provides an efficient device for microbiological transformation of substrates.

Besides the molecular diffusion and flow between the lumen fluid and cell mass, the subject porous wall hollow fiber system provides for hydraulic permeability of the walls to liquids and gases. The fluid flowing through the lumen in the reactor is subject to a pressure gradient, so that there is a pressure drop across the lumen. By introducing the nutrient stream into the lumen at a pressure slightly above the pressure of the fluid in the reactor space external to the hollow fiber, the fluid in the lumen will be expressed through the pores near the entry port of the lumen. By virtue of the pressure drop in the lumen, the pressure at the exit port will be below the pressure of the fluid in the space external to the hollow fiber. Thus, one creates a "radial convective flow," so that the nutrient medium upon entering the lumen is forced into the external space with a high concentration of nutrients, while the fluid in the external space near the exit port is drawn into the lumen with a high concentration of product. The convective flow is capable of carrying nutrients to the cells and metabolites from the cells far more rapidly than would be achieved by diffusion.

Although the foregoing invention has been described in some detail by way of illustration and example for purposes of clarity of understanding, it will be obvious that certain changes and modifications may be practiced within the scope of the appended claims.

What is claimed is:

1. A method for the efficient cultivation of microbial cells employing a microbiological reactor comprising isotropic, porous-wall polymeric hollow-fibers having a cell free zone and a cell containing zone, said cell containing zone substantially located in the space surrounding said hollow-fiber and partially extending beneath the outer surface of said hollow-fibers, wherein both zones are perfused with nutrient medium and separated by a porous barrier permeable to said nutrient medium and impermeable to said cells, said method comprising:

continuously introducing at an entry port of said cell free zone at a pressure greater than the pressure of said nutrient medium in said cell containing zone a nutrient medium stream, whereby said nutrient medium flows out of said cell free zone into said cell containing zone and said microbial cells metabolize nutrients in said nutrient medium to products to produce a product-containing spent nutrient medium in said cell containing zone and said cells further proliferating within said cell containing zone to a cell density greater than $10^{12}$ cell/ml;

continuously flowing said nutrient medium stream remaining in said cell free zone toward an exit port in said cell free zone while reducing the pressure of said nutrient medium stream, so that the pressure of said nutrient medium stream at said exit port is below the pressure of said product-containing nutrient medium in said cell containing zone, whereby product-containing spent nutrient medium in said cell containing zone flows into said cell free zone near said exit port and mixes with said nutrient medium in said cell free zone to form a mixture; and continuously removing said mixture from said exit port of said cell free zone.

2. A method according to claim 1, wherein said porous barrier has a porosity of less than about 50% and pores of a size having as their largest dimension a size less than about 50% of the smallest dimension of said microbial cells.

3. A method according to claim 2, wherein said cell free zone is a plurality of hollow fibers of less than about 1 mm outer diameter.

4. A method according to claim 1, wherein said microbial cells are prokaryotes.

5. A method according to claim 1, wherein said microbial cells are yeast.

6. A method according to claim 1, wherein said microbial cells are fungi.

7. A method according to any of claims 1, or 4, wherein said product includes a polypeptide.

8. A method according to claim 7, wherein said polypeptide is a protein.

9. A method according to claim 8, wherein said protein is an enzyme.

10. A method according to claim 1, wherein said product includes a non-proteinaceous product.

11. A method according to claim 10, wherein said non-proteinaceous product is ethanol.

* * * * *